US012733979B2

(12) United States Patent
Zucker

(10) Patent No.: US 12,733,979 B2
(45) Date of Patent: Sep. 15, 2026

(54) CROSS-MODALITY PLANNING USING FEATURE DETECTION

(71) Applicant: Mazor Robotics Ltd., Caesarea (IL)

(72) Inventor: Ido Zucker, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 1160 days.

(21) Appl. No.: 17/589,951

(22) Filed: Feb. 1, 2022

(65) Prior Publication Data

US 2022/0265352 A1 Aug. 25, 2022

Related U.S. Application Data

(60) Provisional application No. 63/153,513, filed on Feb. 25, 2021.

(51) Int. Cl.

*G06F 7/48* (2006.01)
*A61B 17/70* (2006.01)

(Continued)

(52) U.S. Cl.

CPC .............. *A61B 34/10* (2016.02); *A61B 17/70* (2013.01); *A61B 34/30* (2016.02); *A61B 2034/104* (2016.02); *A61B 2034/105* (2016.02)

(58) Field of Classification Search

CPC ......... A61B 34/10; A61B 17/70; A61B 34/30; A61B 2034/104; A61B 2034/105;

(Continued)

(56) References Cited

U.S. PATENT DOCUMENTS 7,235,076 B2 * 6/2007 Pacheco ............. A61B 17/1671 606/53
10,070,929 B2 9/2018 Tanji (Continued)

FOREIGN PATENT DOCUMENTS

CN 1960680 9/2010
CN 105434047 3/2016

(Continued)

OTHER PUBLICATIONS

Extended Search Report for European Patent Application No. 22156977.5, dated Jul. 27, 2022, 9 pages.

(Continued)

*Primary Examiner* — Nithya J. Moll
(74) *Attorney, Agent, or Firm* — Sheridan Ross PC

(57) ABSTRACT

Systems and methods for planning the position of surgical hardware to be robotically implanted in a subject. The system extracts information about the planned position of hardware from an operative plan based on preoperative images, and converts this information into mathematical vectors. Intraoperatively, at least one three-dimensional scan of the operative site is obtained. The intraoperative images are processed by image analysis, to which are applied artificial intelligence algorithms for feature identification. The vectors derived from the preoperative plan are superimposed on identified anatomical features from the processed intraoperative images. The surgical plan can then be updated intraoperatively, taking into account any shift in position of the anatomical features between the preoperative images and the intraoperative images, prior to robotic insertion of the hardware.

20 Claims, 3 Drawing Sheets

(51) Int. Cl.
*A61B 34/10* (2016.01)
*A61B 34/30* (2016.01)

(58) Field of Classification Search
CPC ........ A61B 2034/102; A61B 2090/374; A61B 2090/376; A61B 2090/3762; A61B 2576/02; A61B 34/20; A61B 2034/107; A61B 2034/108; A61B 2034/2065; G06T 7/12; G06T 7/33; G06T 2207/10081; G06T 2207/10088; G06T 2207/30012; G06V 2201/034
See application file for complete search history.

(56) References Cited

U.S. PATENT DOCUMENTS

| | | | | |
|---|---|---|---|---|
| 10,349,954 | B2 | 7/2019 | Glard et al. | |
| 10,515,449 | B2 | 12/2019 | Miao et al. | |
| 2009/0089034 | A1 | 4/2009 | Penney et al. | |
| 2015/0150523 | A1* | 6/2015 | Sirpad | G06T 15/00 382/132 |
| 2016/0354157 | A1 | 12/2016 | Chen et al. | |
| 2018/0116727 | A1* | 5/2018 | Caldwell | G16H 50/50 |
| 2018/0174311 | A1 | 6/2018 | Kluckner et al. | |
| 2018/0280159 | A1* | 10/2018 | Hunter | A61B 17/1703 |
| 2018/0301213 | A1* | 10/2018 | Zehavi | G06T 7/73 |
| 2019/0142519 | A1 | 5/2019 | Siemionow et al. | |
| 2019/0307513 | A1 | 10/2019 | Leung et al. | |
| 2019/0320995 | A1 | 10/2019 | Amiri | |
| 2019/0380792 | A1 | 12/2019 | Poltaretskyi et al. | |
| 2020/0352651 | A1* | 11/2020 | Junio | A61B 34/10 |
| 2020/0405399 | A1* | 12/2020 | Steinberg | A61B 90/50 |
| 2022/0013211 | A1* | 1/2022 | Steinberg | A61B 34/10 |

FOREIGN PATENT DOCUMENTS

| | | |
|---|---|---|
| KR | 10-1264198 | 5/2013 |
| KR | 10-1547608 | 8/2015 |
| KR | 10-2016-0010092 | 1/2016 |
| WO | WO 2015/130848 | 9/2015 |
| WO | WO 2017/064719 | 4/2017 |
| WO | WO 2018/131044 | 7/2018 |
| WO | WO 2018/131045 | 7/2018 |
| WO | WO 2018/132804 | 7/2018 |
| WO | WO 2018/200767 | 11/2018 |
| WO | WO 2019/051464 | 3/2019 |
| WO | WO 2019/193341 | 10/2019 |

OTHER PUBLICATIONS

Elmi-Terander et al. "Surgical Navigation Technology Based on Augmented Reality and Integrated 4D Intraoperative Imaging," Spine, 2016, vol. 41, No. 21, pp. E1303-E1311.

Esfandiari et al. "A Machine Learning Framework for Intraoperative Segmentation and Quality Assessment of Pedicle Screw X-Rays," EPIC Series in Health Sciences, 2017, vol. 1, pp. 144-150.

Lootus et al. "Vertebrae Detection and Labelling in Lumbar MR Images," MICCAI Workshop: Computational Methods and Clinical Applications for Spine Imaging, Sep. 22-26, 2013, Nagoya, Japan, 12 pages.

Warfield et al. "Real-Time Image Segmentation for Image-Guided Surgery," IEEE, Proceedings of the 1998 ACM/IEEE SC 98 Conference (SC'98), 1998, 13 pages.

Extended Search Report for European Patent Application No. 24221570.5, dated Mar. 14, 2025, 8 pages.

Official Action with English Translation for China Patent Application No. 202210177195.1, dated May 27, 2026, 30 pages.

* cited by examiner

CROSS-MODALITY PLANNING USING FEATURE DETECTION

CROSS REFERENCE TO RELATED APPLICATIONS

This application claims the benefit of U.S. Provisional Application No. 63/153,513, filed on Feb. 25, 2021, and entitled "Cross-Modality Planning Using Feature Detection," which application is incorporated herein by reference in its entirety.

FIELD

The present disclosure describes technology related to the field of robotic surgery, especially for increasing the accuracy of a pre-planned orthopedic procedure without the need for external registration.

BACKGROUND

In orthopedic and neurosurgical procedures, a surgical procedure may be preplanned based on preoperatively acquired three-dimensional MRI or CT images. This plan may comprise the number, size, position and orientation of hardware to be inserted during the procedure. Intraoperatively, the surgical team must apply the preoperative or intraoperative plan, based on the virtual images, to the actual spine of the patient. Thus, some means must be employed to convert the planned position of intervertebral rods, pedicle screws, and other hardware from the preoperative plan to the patient.

In operations performed by robotic insertion of the instrumentation, this conversion is typically accomplished by means of registration, whereby an external coordinate system is used to align the planned position of the implanted hardware with the patient's anatomy. The operation is then accomplished by surgical tools under the control of a robotic controller, which is configured to store the coordinate system of both the robotic arms and the operative plan. Alternately, preoperative images may be omitted; in this case, registration may be accomplished by taking an intraoperative image set while the patient is positioned on the table before the operation begins. The surgeon then plans the procedure based on the intraoperative image set, which is aligned with the current anatomical positioning of the bones to be instrumented, and the robotic co-ordinate system is correlated to the intraoperative image set by one of the known registration methods.

Registration methods to align a preoperative image set with at least one image taken intraoperatively typically use intensity-based algorithms, such as those which seek to maximize information-theoretic similarity measures. These techniques assume a relationship between the intensities in one image and those in the corresponding regions of another image for mapping one intensity map to another. However, this assumption is often not reliable in a situation where different imaging methods that exploit different physical properties are used to obtain an image of the same anatomical region.

Another approach to registration is referred to as feature-based registration, in which the input images are first reduced to simpler geometric representations (such as a set of points or surfaces) and these geometric representations are then registered with one another. This approach typically involves identifying corresponding features, such as anatomical landmark points and tissue boundaries in each image. The process of extracting features from image data, known as image segmentation, can be performed manually or with the use of segmentation software. Performed intraoperatively, this method may be limited both by the lower quality of the intraoperative images and by the time required for the alignment process.

The accuracy of registration, accomplished by any number of means, may commonly range from 2-4 mm difference between the three-dimensional images and the patient's anatomical features. For operations in which the bones to be instrumented are large, such a degree of accuracy may suffice. However, for robotic insertion of a pedicle screw into a vertebra, for example, an incorrect deviation of a few millimeters may result in the patient suffering irreversible neurological damage. Thus, methods of improving the accuracy of surgical robotic instrumentation, especially for spinal operations, are sought.

Reference is made to the following documents:

Vertebrae detection and labelling in lumbar MR images. Lootus M, et al., MICCAI Workshop: Computational Methods and Clinical Applications for Spine Imaging. Sep. 22-26, 2013, Nagoya, Japan.

WO 2018/131044 Dynamic motion global balance, by Shoham M and Steinberg S, filed 11 Jan. 2018, and assigned to Medtronic, Inc.

WO 2017/064719 Global Spinal Alignment Method, by Zehavi E, et al., filed 13 Oct. 2016, and assigned to Medtronic Inc.

SUMMARY

The present disclosure describes new exemplary systems for cross-modality planning of spine procedures without registration. The disclosed methods may be performed either immediately or pre-operatively, and provides the surgeon with the ability to preplan the case, improving the outcome and efficiency of the operation. Preplanning of instrumentation once the patient is on the operating table, or using the presently disclosed methods, up to a week or longer prior to the operation. Having the option to design the operative procedure prior to the date of surgery allows the surgeon to know in advance how many and what kind of pedicle screws, intervertebral rods, or other hardware will be needed. This saves time on the day of the operation, thus allowing for better inventory control and lowering operating room costs.

When planning a spinal surgical procedure, the surgeon may use different imaging modalities, each having its advantages and limitations. MRI is advantageous in visualizing soft tissues, whereas CT is optimal for bone, and X-ray fluoroscopy provides relative low radiation and high accessibility. In order to execute a pre-operative plan in the operating room, registration of the preoperative images with the intraoperative images must first be achieved. Due to the variety of modalities and scan protocols, enabling these registrations proves to be challenging, in addition to the challenges in alignment due to minor shifts in the comparative positions of anatomical features between the two sets of images. A major problem in performing registration between preoperative and intraoperative images arises from the significant difference in resolution and clarity between the two modalities. The preoperative images, usually CT or MRI images, have a higher resolution and clarity than intraoperative images, even if those intraoperative images are from sets of images generated by rotary, multi-plane, fluoroscope systems, which generate CT-type three-dimensional image sets, such as the O-Arm imaging system supplied by Medtronic. Since surgical plans are generally developed using preoperative, high definition, 3D image sets, there is a need to register the images on which the surgical plan is based with the intraoperative images, since, in the absence of a registration routine, the robotic coordinate system is directly correlated only with the intraoperative images. Another problem to be solved is that image registration depends on identification of the same features in two sets of images, which may be obtained with different imaging systems and use different processing algorithms.

Exemplary systems of the present disclosure use a method of enabling the well-resolved and comparatively detailed preoperative 3D images to be used to enable any spatial surgical feature, planned on the preoperative image set, to be defined on intraoperative images taken in the operating room. This method therefore achieves the goal of relating the intraoperative image features to the preoperative detail, without the need to perform a rigorous image registration between the preoperative images and the intraoperative images. The system and methods are particularly applicable when a well-defined feature, such as surgical hardware like a pedicle screw, is the feature of interest whose position intraoperatively must be determined accurately.

Each component of the hardware denoted in the surgical plan has a three-dimensional pose, defined as position, angular direction or orientation, and length. This three-dimensional pose and length may be defined as a mathematical vector or vectors, with the sum of mathematical vectors for one or more two- or three-dimensional hardware elements, such as a pair of pedicle screws for a single vertebra, hereafter referred to as a three-dimensional assembly. The pre-operative plan may be expressed as the combination of all three-dimensional assemblies for the full complement of hardware to be inserted, such as pedicle screws and intervertebral rods for all the vertebrae to be instrumented or fused. Individual three-dimensional assemblies may be superimposed on the same anatomic feature as displayed in a three-dimensional image generated intraoperatively. Since the three-dimensional assemblies are known accurately from the surgical plan based upon the well-resolved preoperative images, such assemblies may be used as "markers" having immutable positions and orientations. Such a marker can then be imposed onto a three-dimensional intraoperative image of the relevant feature into which the hardware components of the assembly are to be implanted, using as guidance, known limitations of the desired position of the implant assembly in the anatomical feature. If the accuracy of the imposition is acceptable, as will be expounded below, then that position of the implant assembly can be regarded as an accurate reflection in the intraoperative images, of the original position of the implant assembly according to the surgical plan derived from the preoperative images. Once a number of such impositions have been performed for neighboring anatomic elements, a decision can be made as to whether the impositions of all of the three-dimensional implant assemblies is acceptably accurate. This can be achieved by reviewing whether adjacent implant assemblies have essentially the same mutual alignments, within a predetermined margin, as those of the equivalent implants in the preoperative image surgical plan. If any diversion beyond the predetermined margin is observed, that can be taken as a sign that one of the impositions of an implant assembly into its intended anatomic element, such as a vertebra, is inaccurate, and the imposition procedure should be repeated, by iterative adjustments of the position of the iterant three-dimensional assembly, or group of assemblies. This readjustment of the imposed position is repeated iteratively, until an acceptably accurate match of the alignments of all adjacent assemblies with their preoperative alignments, has been obtained.

A useful illustration of this concept applies to the common procedure of inserting pedicle screws into vertebrae for a spinal fusion instrumentation. In this exemplary implementation, a pair of two pedicle screws to be inserted into a particular vertebra is denoted as a three-dimensional assembly representing the intended poses and lengths of the two pedicle screws together. Intraoperatively, typical pedicle screw poses are independently determined on the segmented intraoperative images. The three-dimensional assembly is then superimposed onto segmented, three-dimensional image sets of that vertebra acquired intraoperatively, and the preoperative paired three-dimensional assembly of two screws is compared with the intraoperatively determined individual screw positions. If both sets of planned screw positions fit the intraoperative images, the operation may proceed without alteration. If a discrepancy between the two planned positions is identified, then the system must adjust the planned pose of at least one of the intraoperatively determined screw poses.

The method of comparing screw pair positions in order to relate features in an intraoperative image to the equivalent features in a preoperative image set, is based on the increased facility and accuracy with which it is possible to correctly position a three-dimensional coordinate-defined feature, such as pair of screws or a surgical insert assembly, into a single vertebra into which it is to be implanted, rather than in trying to relate the complete three-dimensional vertebra from the preoperative image set with the intraoperative image set by means of one of the registration procedures known in the art.

As mentioned, one example of such use is in the verification of the above-mentioned positioning of pedicle screws used in the fixation of spinal fusion rods, to ensure that the planned screw positions do not intrude into any sensitive neural or muscular or vascular regions, thereby causing serious damage. Another example could be in the definition of the position and extent of a resection of a laminar portion of the vertebra, this position and extent being clearly defined in the preoperative image plan, and now needing to be transferred to an intraoperative image of the region of the spine of the patient, on which the surgical process is being performed. In this case, the plane of the lamina section to be removed from a single vertebra, or more accurately, a line perpendicular to the plane of the lamina section, and the width of the resected part, can be used to outline the three-dimensional, coordinate-defined shape for superimposing on the intraoperative images of that vertebra.

Embodiments of the disclosed methods allow for converting the planned hardware poses from the preoperative surgical plan into a three-dimensional assembly comprising, in one exemplary implementation, the pose and length of each pedicle screw, or the pose, length and curvature of a pair of intervertebral rods. In the case of a spinal fusion, which is used as an exemplary implementation of the present disclosure, each pair of pedicle screws or each set of two intervertebral rods defined in the surgical plan, is converted into a single three-dimensional assembly defined by the three-dimensional positions of a pair of pedicle screws or set of rods. A separate three-dimensional assembly is calculated for each set or pair of hardware elements that remains constant in relation to a specific bony element such as a vertebra. The complete group of three-dimensional assemblies for all of the vertebrae in the region of the spine being treated, represents the total preoperative information about the planned pedicle screw lengths, spatial locations and their angular orientations, or about the set of intervertebral rods. These three-dimensional assemblies provide complete spatial information of the intended position of the pedicle screws or intervertebral rods in the preoperative images, according to the surgical plan. In some implementations, a first pair of pedicle screws is used after implantation in combination with at least one processed intraoperative three-dimensional image to accomplish the alignment of the second pair of pedicle screws.

One problem to be solved by some embodiments of the present disclosure is how to superimpose the preoperative screw poses and lengths onto the intraoperatively generated three-dimensional images, without the need to perform the complicated task of registration of images of the complete region of interest of the spine. This is achieved in implementations of the methods of the present disclosure, by first performing segmentation of the intraoperative images in the region of interest of the spine. Although such intraoperative images do not have the same resolution or image quality as the preoperative images, after image segmentation, the system is able to consider each vertebra as a separate feature, rather than the more difficult task of considering the entire spinal section as a unit. The system can then use signal processing methods, including feature detection algorithms, based on artificial intelligence and database-derived shape expectations where necessary, to regenerate from the three-dimensional intraoperative images, with high accuracy, the three-dimensional surface profile of each separate vertebra, including the pedicles, the lamina and the vertebral body. By using artificial intelligence, and aggregate or compiled information from a database, such regeneration can be performed even when parts of the vertebra shape may be unclear or occluded. Once the three-dimensional surface shape has been computed for a given vertebra, the three-dimensional assembly corresponding to the pair of pedicle screws for that vertebra, as imaged preoperatively, can be manipulated as a single unit, and superimposed as a unit onto the intraoperative three-dimensional image outline of the vertebra.

In performing this manipulation, the system controller or computing module applies criteria to determine the reliability of the superposition of each three-dimensional assembly comprising a screw pair into its intraoperatively imaged vertebra. In some embodiments, the following conditions should be fulfilled for the positioning of each three-dimensional assembly onto the segmented intraoperative image of its respective vertebra:

- the trajectory of neither screw will violate the paraspinal muscles or the spinal canal,
- the starting position of each pedicle screw entry point, representing the base of the head of the screw, is on the surface of the pedicle bone, and
- the distal tip of each pedicle screw will not violate the vertebral endplates or extend beyond the anterior edge of the vertebral body.

This manipulation procedure is repeated separately for each of the vertebrae to which pedicle screws are to be applied.

The above procedure ensures that the three-dimensional assembly representing each pair of pedicle screws is correctly superposed onto the intraoperative image of each vertebra, in that:

(i) each vector of the vector pair represents an acceptable and safe position for a pedicle screw, and (ii) each three-dimensional assembly superposed on the intraoperative outline image of the vertebra, is a faithful representation of the original vector pair accurately imaged in the higher quality preoperative image set, such that each pedicle screw retains its original position and orientation relative to the other pedicle screw of the same pair.

At this point, the assembly of regenerated intraoperative vertebral images are now considered as representing the complete virtual construct, or at least the complete set of pedicle screw poses for the construct applied to the instrumented region of the spine. These poses are to be used intraoperatively in order to provide instructions for the accurate drilling of the pedicle screw holes. However, before embarking on a surgical step on the subject, and in the absence of a formal registration step of the preoperative screw positions with the calculated intraoperative positions, it is necessary to confirm that the iterative manipulation of the three-dimensional assemblies of all of the pedicle screw pairs has been correctly performed, and that the resulting pedicle screw holes are safe to execute. In order to confirm this, a construct validity procedure is followed. This is based on the assumption that any differences between the preoperative and the intraoperatively calculated vertebra positions should be slight, unless the algorithm has identified a cost function minimum incompatible with the subject's anatomy.

Exemplary methods of the present disclosure also take into consideration the total number of vertebrae to be instrumented and the full set of hardware to be inserted, such that each three-dimensional assembly corresponding to the intended pedicle screws of a single vertebra are planned within the limitations of all allowable angles in a global preoperative model for the entire spinal segment to be instrumented, as represented by all three-dimensional assemblies for all of the relevant vertebrae. Because the position of each vertebra relative to the adjacent vertebrae may change between preoperative and intraoperative positions of the subject's spine, implementations of the disclosure may be used to compare the position of each element of the entire hardware assembly in both preplanned and intraoperative stages. Once all of the three-dimensional geometric shapes having the pedicle screw positions for each vertebra to be instrumented have been positioned on the intraoperative images, a comparison may be made between the initially planned bone-hardware assembly comprising intervertebral rods and pedicle screws, and the current intraoperative version. Any identified differences or shifts may thus be identified. On the intraoperative version of the bone-hardware assembly, spinal alignment parameters can be measured and compared to those from the preoperative surgical plan, and any needed corrections made in the planned screw positions.

The same method of vector positioning and analysis may be applied to all spinal screws (pedicle, trance, lamina), as well as to decompression or other types of preoperative plans for hardware insertion, whether spinal or other orthopedic or neurosurgical procedures.

Cost function, or loss function, is a function that measures the performance of a machine learning model for given data. Cost function quantifies the error between predicted/expected values and actual values, and can be formed in many different ways. In the present application, cost function is applied to the predicted vs. actual alignment of the three-dimensional geometric function representing a pair of pedicle screws onto the processed intraoperative image of the vertebra into which the screws are to be implanted.

Finite element analysis (FEA) is a numerical method for solving equations in two or three space variables by subdividing a large system into smaller, simpler parts that are called finite elements. FEA is used in image analysis to reduce the degrees of freedom from infinite to finite with the help of discretization or meshing. Once defined elements of an image have been identified, a pair of images, in this case preoperative and intraoperative, can be compared by superpositioning one meshed image on another.

Image segmentation is the process of partitioning a digital image into multiple segments (sets of pixels, also known as image objects). The goal of segmentation is to simplify and/or change the representation of a complex image into something that is more meaningful and easier to analyze.

Three-dimensional assembly is the term used to identify the planned position, orientation, and lengths of a set of hardware to be implanted during a procedure; in the exemplary implementation discussed, a pair of pedicle screws for a given vertebra is converted into a fixed shape quantitatively defining the screw poses in three-dimensional space. The sum total of hardware elements to be implanted may be defined by a series of three-dimensional arrays.

Registration defines the process of transforming different sets of data into a common coordinate system; in this application, a preoperative image set is aligned with at least one intraoperative image of a patient's anatomy, for the purpose of the robotic controller instructing the robotic arm to carry out a surgical step on the imaged anatomy.

Example aspects of the present disclosure include:

A system for co-relating a preoperative image-based surgical plan for instrumentation to intra-operative images comprises: at least one processor executing instructions stored on at least one non-transitory storage medium, to cause the at least one processor to: a) based on a surgical plan derived from a preoperative image set, define planned poses for at least one three-dimensional implantable hardware element, or at least two two-dimensional implantable hardware elements, for an anatomical part to be instrumented; b) convert the planned poses into a three-dimensional geometric function for the anatomical part to be instrumented; c) process at least one intraoperative three-dimensional image of the anatomical part to be instrumented to identify anatomical features to which the three-dimensional geometric function is to be aligned; d) on the processed intraoperative image, define a range of possible positions for the three-dimensional geometric function; and e) using the identified anatomical features, virtually align the three-dimensional geometric function in the at least one processed intraoperative three-dimensional image, the alignment achieving a position of the implantable hardware elements that is compatible with the surgical plan and has greater accuracy than aligning each hardware element individually on the intraoperative image, without the need to perform registration between the preoperative and intraoperative images.

Any of the aspects herein, wherein steps a) to e) are performed on a plurality of anatomical parts to be instrumented.

Any of the aspects herein, further comprising steps: f) repeat steps a) to e) on each anatomical part to be instrumented, such that a plurality of three-dimensional geometric functions is generated; g) compare virtual alignments from the at least one intraoperative image of all three-dimensional geometric functions with the preoperative surgical plan; and h) if the alignments on the at least one intraoperative image are inconsistent with the preoperative surgical plan, repeat step e), such that the positioning of the implantable hardware elements has greater accuracy than aligning each hardware element individually on the intraoperative image for a complete set of implantable hardware elements for the sum of anatomical parts to be instrumented.

Any of the aspects herein, wherein a robotic surgical system enabled to carry out the surgical plan uses at least one aligned three-dimensional geometric function in the at least one processed three-dimensional intraoperative image to update the surgical plan.

Any of the aspects herein, wherein the preoperative image-based surgical plan is planned from at least one three-dimensional MRI or CT image set.

Any of the aspects herein, wherein positioning the three-dimensional geometric functions may be based on one or more predetermined constraints corresponding to the anatomical features.

Any of the aspects herein, wherein the surgical plan is for a spinal fusion, the hardware elements are pedicle screws and intervertebral rods, and the anatomical parts are vertebrae.

Any of the aspects herein, wherein the three-dimensional geometric function defines a fixed angle between the at least two two-dimensional implantable hardware elements in reference to each other.

Any of the aspects herein, wherein at least one form of artificial intelligence and anatomical images are used to identify a range of possible positions for implantable hardware elements within the at least one three-dimensional intraoperative image.

Any of the aspects herein, further comprising the step of determining a mismatch in the planned poses of implantable hardware elements between the preoperative image-based surgical plan, and the at least one processed intraoperative image, wherein the determined mismatch is used to adjust the planned poses of the implantable hardware elements.

Any of the aspects herein, wherein reducing the stress cost function is determined using an algorithm that identifies a stress minimum between the at least one implantable hardware element and the anatomical part into which it is to be implanted.

Any of the aspects herein, wherein the algorithm uses artificial intelligence applied to at least one of feature detection, intensity detection, finite element analysis with meshing, and image segmentation to reduce the stress cost function.

Any of the aspects herein, wherein the three-dimensional geometric functions for all implantable hardware elements are positioned in combination with analysis of preoperative images showing motion analysis of the anatomical parts to be instrumented.

Any of the aspects herein, wherein the plan for instrumentation is a spinal fusion, and the optimal position of the plurality of implantable hardware elements is determined by analysis of measured spinal mobility limitations over substantial lengths of the patient's spine in order to plan a correction procedure with minimal surgical corrective steps.

Any of the aspects herein, wherein the three-dimensional geometric function is defined as a mathematical quantity having four points, the four points representing the beginning and ending of each of a pair of pedicle screws for a given vertebra in three-dimensional space.

Any of the aspects herein, wherein a first of the pair of pedicle screws is used after implantation in combination with the at least one processed intraoperative three-dimensional image to accomplish the alignment of the second of the pair of pedicle screws.

Any of the aspects herein, wherein the stress cost function further takes into account the predicted stress of all implantable hardware elements on all anatomical parts to be instrumented.

Any of the aspects herein, wherein the three-dimensional geometric function comprises the position, length, and angle of a right pedicle screw and a left pedicle screw having a fixed angle between them, for implantation into a single vertebra.

Any of the aspects herein, wherein the alignment achieving a reduced stress cost function of the plurality of implantable hardware elements further takes into account anatomical elements to be avoided, for example nerves, blood vessels, and muscles.

A system for aligning a planned position of surgical hardware from preoperative images of a subject onto images obtained intra-operatively comprises a memory for storing a surgical plan, based on preoperative images, on a region of interest, the surgical plan comprising planned positions of hardware to be inserted into anatomical features in the region of interest, and at least one processor having a controller, configured to identify the anatomical features in the region of interest in intraoperative images of the subject, wherein the system is configured to convert the planned positions of hardware into vectors, and to superimpose a pair of vectors representing two hardware elements in a fixed relationship to each other, onto the anatomical features identified in the intraoperative images, such that the surgical plan can be updated intraoperatively taking into account any shift in position of the anatomical features between the preoperative images and the intraoperative images.

Any of the aspects herein, wherein each vector represents a pedicle screw, and the anatomical features represent aspects of at least one vertebra.

Any of the aspects herein, wherein the vectors have a specific length and pose in reference to the vertebra and to each other.

Any of the aspects herein, wherein the anatomical features are identified with algorithms using artificial intelligence applied to at least one of feature detection, intensity detection, finite element analysis with meshing, and image segmentation to identify anatomical features.

Any of the aspects herein, wherein updating the surgical plan takes into account the full complement of hardware to be inserted and the desired outcome for all vertebrae.

A method of aligning a planned position of surgical hardware from preoperative images onto images obtained intra-operatively comprises a) based on a surgical plan derived from a preoperative image set, defining planned poses for at least one three-dimensional implantable hardware element, or at least two two-dimensional implantable hardware elements, for an anatomical part to be instrumented; b) converting the planned poses into a three-dimensional geometric function for the anatomical part to be instrumented; c) processing at least one intraoperative three-dimensional image of the anatomical part to be instrumented to identify anatomical features to which the three-dimensional geometric function is to be aligned; d) on the processed intraoperative image, defining a range of possible positions for the three-dimensional geometric function; e) using the identified anatomical features, virtually aligning the three-dimensional geometric function in the at least one processed intraoperative three-dimensional image, the alignment achieving a position of the implantable hardware elements that is compatible with the surgical plan and has greater accuracy than aligning each hardware element individually on the intraoperative image; f) repeating steps a) to e) on a plurality of anatomical parts to be instrumented, such that a plurality of three-dimensional geometric functions is generated; g) comparing virtual alignments from the at least one intraoperative image of all three-dimensional geometric functions with the preoperative surgical plan; and h) if the alignments on the at least one intraoperative image are inconsistent with the preoperative surgical plan, repeating step e), such that the positioning of the implantable hardware elements has greater accuracy than aligning each hardware element individually on the intraoperative image for a complete set of implantable hardware elements for the sum of anatomical parts to be instrumented.

Any of the aspects herein, wherein a robotic surgical system is enabled to carry out the surgical plan using the aligned three-dimensional geometric functions in the at least one processed intraoperative three-dimensional image without reference to the preoperative images.

A system for aligning a pair of pedicle screws to intraoperative images of the vertebra into which the screws are to be inserted comprises at least one processor executing instructions stored on at least one non-transitory storage medium, to cause the at least one processor to: a) based on a surgical plan derived from a preoperative image set, define planned poses of a pair of pedicle screws for a vertebra to be instrumented; b) convert the planned poses of the pair of screws into a three-dimensional geometric function; c) process at least one intraoperative three-dimensional image of the vertebra to outline surface features of the vertebra; d) on the processed intraoperative image, define a range of possible positions for each pedicle screw through the vertebral pedicles; and e) using the identified anatomical features, virtually align the three-dimensional geometric function in the at least one processed intraoperative three-dimensional image, the alignment achieving a position of the pedicle screws that is compatible with the surgical plan and reduces a cost function to a greater degree than aligning each pedicle screw individually on the intraoperative image.

A system for aligning a pair of pedicle screws to intraoperative images of the vertebra into which the screws are to be inserted comprises at least one processor executing instructions stored on at least one non-transitory storage medium, to cause the at least one processor to: a) based on a surgical plan derived from a preoperative image set, define planned poses of a pair of pedicle screws for a vertebra to be instrumented; b) convert the planned poses of the pair of screws into a three-dimensional geometric function; c) process at least one intraoperative three-dimensional image of the vertebra to identify anatomical features or outline surface features of the vertebra; d) on the processed intraoperative image, define a range of possible positions for each pedicle screw through the vertebral pedicles; and e) using the identified anatomical features, virtually align the three-dimensional geometric function in the at least one processed intraoperative three-dimensional image, the alignment achieving a position of the pedicle screws that is compatible with the surgical plan and has greater accuracy than aligning each pedicle screw individually on the intraoperative image.

Any of the aspects herein, further comprising the steps: f) repeat steps a) to e) on all vertebrae to be instrumented; g) align all vertebrae to be instrumented, each with its pair of pedicle screws positioned according to step e), with all three-dimensional geometric functions defined in step b); h) identify the difference between each three-dimensional geometric function as defined in step b) with the aligned vertebrae in step g); and i) if one or more pairs of screw positions in step g) differ from the positions determined in step b) by more than a predetermined amount, iteratively recalculate the screw positions until the difference between the recalculated screw positions and the surgical plan is less than the predetermined amount.

A system for aligning a pair of pedicle screws to intraoperative images of the vertebra into which the screws are to be inserted comprises at least one processor executing instructions stored on at least one non-transitory storage medium, to cause the at least one processor to: a) based on a surgical plan derived from a preoperative image set, define planned poses of a pair of pedicle screws for a vertebra to be instrumented; b) convert the planned poses of the pair of screws into a three-dimensional geometric function; c) process at least one intraoperative three-dimensional image of the vertebra to outline surface features of the vertebra; d) on the processed intraoperative image, define a range of possible positions for each pedicle screw through the vertebral pedicles; and e) using the identified anatomical features, virtually align the three-dimensional geometric function in the at least one processed intraoperative three-dimensional image, the alignment achieving a position of the pedicle screws that is compatible with the surgical plan and reduces a cost function, without the need to perform registration between the preoperative and intraoperative images.

Any of the aspects herein, wherein the cost function is a feature of a machine learning model used to find a best fit between the three-dimensional geometric function and the processed intraoperative image of the vertebra, and the best fit is determined by linear regression.

Any of the aspects herein, further comprising: f) repeat steps a) to e) on all vertebrae to be instrumented; g) align all vertebrae to be instrumented, each with its pair of pedicle screws positioned according to step e), with all three-dimensional geometric functions defined in step b); h) identify the difference between each three-dimensional geometric function as defined in step b) with the aligned vertebrae in step g) using the machine learning model; and i) if one or more pairs of screw positions in step g) differ from the positions determined in step b) by more than a predetermined amount, iteratively recalculate the screw positions until the difference between the recalculated screw positions and the surgical plan is less than the predetermined amount.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The present invention will be understood and appreciated more fully from the following detailed description, taken in conjunction with the drawings in which.

DETAILED DESCRIPTION

Figure 1:
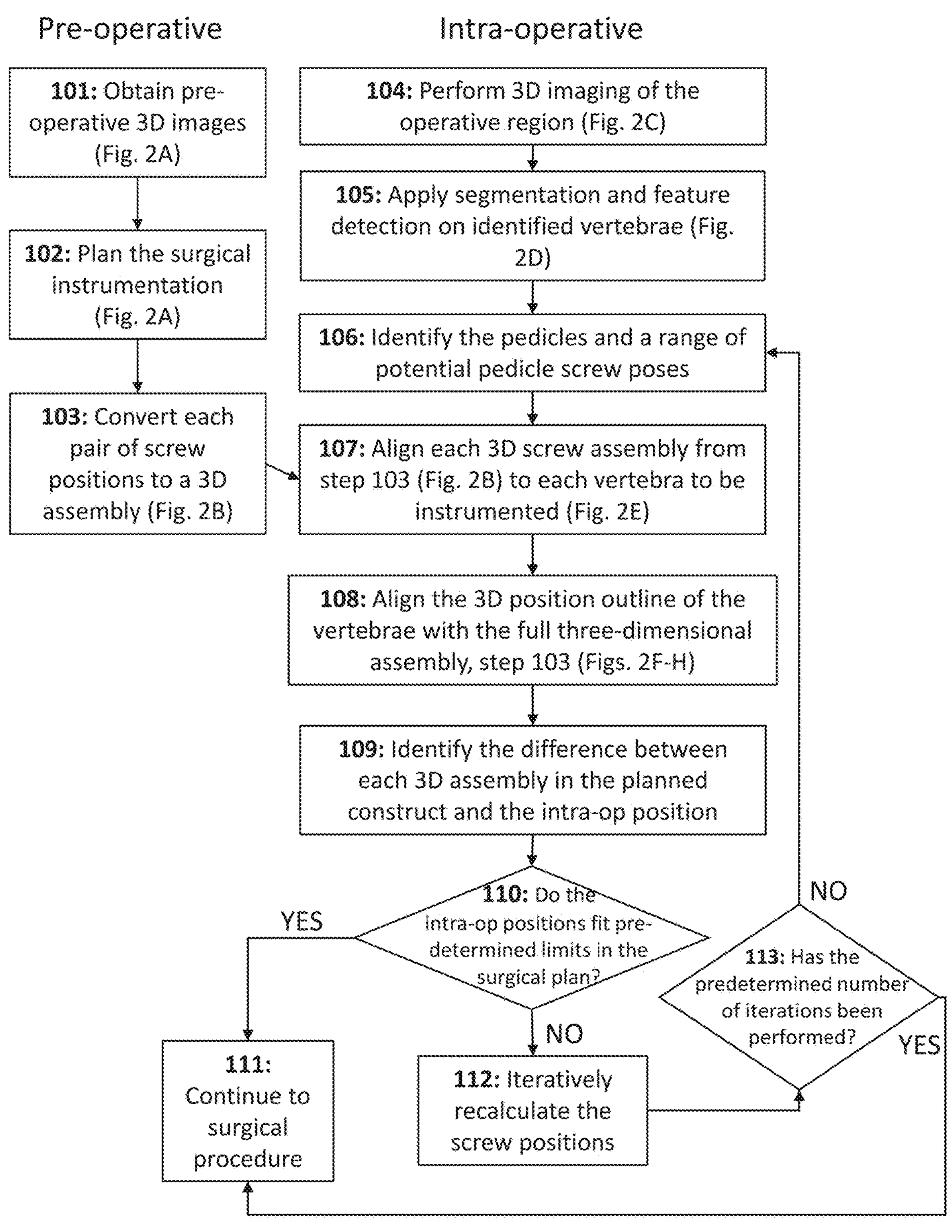
FIG. 1 shows a flow chart with the steps of a typical implementation of the disclosed methods.

Reference is now made to FIG. 1, which illustrates schematically an overview of the procedure followed in an exemplary implementation of the present disclosure, applying the method to a spinal fusion. In step 101, a preoperative three-dimensional image set is obtained of at least the operative region of the subject. Examples of such image sets could be CT or MRI image sets.

In step 102, the surgeon or operator plans the surgical instrumentation. In the exemplary case of an L3-L5 lumbar spinal fusion, the instrumentation may comprise two intervertebral rods on either side of the L3, L4, and L5 spinal processes, each rod attached to the L3-L5 vertebrae via three sets of pedicle screws, one set into each vertebra. The surgical plan should include the type, size, shape, composition, and other relevant characteristics of each piece of hardware to be inserted, including the intended position of each rod relative to the vertebrae into which it will be implanted, and the positions of the screws for affixing the rod.

In step 103, the positions and orientations of the left and right screws for a given vertebra to be instrumented are converted to a rigid body or three-dimensional assembly maintaining the fixed angle and distance between the two screws, each of which has a defined diameter and length. The three-dimensional assembly represents the combined three-dimensional pose and length of each of the pair of pedicle screws for a given vertebra.

Extracting the essential information about the paired screw positions into a single three-dimensional quantity allows more precise matching of the identified features of the vertebra in intraoperative images with the preoperatively determined screw positions by fixing the position of two hardware elements relative to each other and relative to a single anatomical element, i.e., vertebra, into which they are to be implanted. By extracting the essential information from the preoperative image set and converting the paired screw positions to a rigid three-dimensional quantity, it eliminates the need to register anatomical elements from the preoperative images with the intraoperative images. Thus, any set of preoperative MRI or CT images is usable, without concern that they were obtained by a different system compared with the intraoperative images. The method may be applied to hardware elements other than pedicle screws.

In addition to converting each pair of vertebral pedicle screws into a three-dimensional assembly, the sum of all three-dimensional assemblies comprising the full set of paired screw positions for the entire set of screws to be inserted is arranged in three-dimensional space, each screw segment in its desired pose in relationship to the spinal column, and corresponding to the final, planned bone-hardware assembly. The complete assembly allows an intraoperative comparison between the preoperative plan and the intraoperative screw positions for each vertebra. Any discrepancy between the actual intraoperative positions of all relevant vertebrae in the patient and the paired screw positions from the preoperative plan can be identified and corrected, either by adjusting the planned screw positions or by adjusting the position of one or more vertebrae to be instrumented.

Whereas an embodiment of the present disclosure uses pedicle screws as exemplary elements of the hardware to be modeled as three-dimensional segments, other components such as intervertebral rods may also be modeled as three-dimensional shapes in a three-dimensional array. The necessity for both paired three-dimensional arrays for a given vertebra and full arrays of all hardware is explained in further detail in step 108 herewithin below.

Intraoperatively, in step 104, a three-dimensional volume scan using an imaging modality such as CT or MRI, or possibly AP and lateral fluoroscope images, is performed of the operative region; in this example, encompassing at least L3-L5. The image is performed with the patient in the operative position on the operating table, such that the spinal elements are in the pose that they will be in during the procedure.

In step 105, the three-dimensional intraoperative image is subjected to image segmentation to identify vertebral features. These features could be some or any of bony protuberances such as the transverse processes and spinal processes; vertebral end plates; and the vertebral laminae and pedicles. With the information gathered, the system uses the identified features of an individual vertebra to generate a three-dimensional outline of the bone. In some implementations, the images are processed using artificial intelligence to identify and detect specific features on the processed images, using machine learning, deep learning, neural networks, or other types of computer learning. Finite element analysis with meshing may be employed to define the boundaries of anatomical features, primarily bones.

In step 106, based on the three-dimensional outline of the vertebra, typical positions for the pedicle screws are identified bilaterally in the segmented intraoperative image. This step is performed without reference to the three-dimensional assembly calculated in step 103. The system identifies the position and geometry of the pedicles and the lamina on the intraoperative scan. Based on the unique three-dimensional shape of the segmented bone, the system then determines an initial range of screw poses, a task which in the case of a vertebra is further enabled by the narrow dimensions of the pedicle. The inserted screws must enter at an entry point and angle, such that the tip and shaft of the screw pass through the narrow vertebral pedicle, avoiding both the spinal canal medially and the paraspinal muscles laterally, and the vertebral endplates superiorly and inferiorly. This step may be performed without reference to the preoperatively determined three-dimensional paired pedicle screw arrays, and the position of each pedicle may be determined either individually or as a pair.

In step 107, each three-dimensional assembly from step 103, representing a pair of pedicle screws for a given vertebra, is separately aligned with the three-dimensional outline of the corresponding segmented vertebra from the processed intraoperative image in step 105, within the range of potential screw positions determined in step 106. The system positions the individual pedicle screws according to the limitations of the segmented volume, i.e., inside the pedicle, with the head of the screw touching the lamina, and the tip of the screw not extending beyond the vertebral body. The system or algorithm further takes into account a minimization of stress as identified by a cost function. Because each screw must traverse a path within the vertebral pedicle, and each pedicle is oriented in a specific orientation with respect to the vertebral body, the angles of the screws from the preoperative plan remain stable with respect to the individual vertebra. Only a single or very small range of positions will provide an optimal or correct positioning for both of the pair of pedicle screws that also fulfills the condition of reducing the cost function.

In step 108, the full set of pre-operative three-dimensional hardware assemblies is overlaid on the segmented intraoperative image of the spine, the superimposition showing both the pairs of pedicle screw positions determined in step 107, and the three-dimensional position of the sum of all pairs of pedicle screws as planned pre-operatively. This step is a check to ensure that the algorithm has correctly identified the lowest cost function. Ideally, the alignment of screw positions in individual vertebrae in step 107 matches the alignment of the full complement of hardware in step 108, such that the original three-dimensional assemblies based on the preoperative plan, and the updated screw positions based on the intraoperative images, are coincident. However, in some cases, the algorithm may identify a reduced cost function for one of the screw positions in one vertebra that is incompatible with the anatomical map of vertebrae in the three-dimensional images.

A mismatch identified when the preoperative three-dimensional assembly array is overlaid on the intraoperative image could indicate that the algorithm has identified an anatomically incompatible stress function and should be corrected. In step 109, any deviations in the position of screw pairs for one vertebra may be identified and corrected based on the preoperative three-dimensional assembly. The delta, if any, is determined between each three-dimensional assembly representing a pair of pedicle screws from step

107, and the complete three-dimensional array representing the complete bone-hardware assembly overlaid on the intra-operative vertebral positions.

Based on the desired vertebral positions and angles from the preoperative plan designed from the preoperative image, and according to a defined set of parameters, the system determines for each vertebra the most accurate final bone-implant assembly. The location of each pair of pedicle screws is positioned independently inside a vertebra according to anatomical recognition and the pre-operative plan. However, if, after independently positioning the pedicle screw assemblies for two adjacent vertebrae, a large axial angle shift is identified between them in the full hardware assembly, the intraoperative super-positioning process may have been inaccurate and will need to be updated. Whereas a small coronal angular alignment difference of 2° to 3° between a pair of adjacent vertebrae may be acceptable, possibly arising from approximations in the reconstructed vertebral shape, any larger angular difference between the two vertebrae would mean that the vertebral shape reconstructed from the intraoperative images was not accurate, and was perhaps due to the iterative reconstruction optimization procedure converging onto an incorrect minimum. The same process would apply to unacceptably large axial rotations between adjacent vertebrae.

In step 110, the system evaluates whether the intraoperatively determined screw positions are compatible with the global instrumentation plan, ensuring that the screw angle does not change more than a predetermined amount from the allowed model. The allowed model may be determined with the assistance of other disclosures assigned to the current applicant, such as PCT/IL2018/050052 Global Balance Using Dynamic Motion Analysis, and PCT/IL2016/051121 Global Spinal Alignment Method, both of which are incorporated by reference. If the screw angles remain in the allowable range according to the preoperative model, the method proceeds to step 111 and the surgical procedure is carried out. If not, in step 112 the screw positions are corrected in the intraoperative images, based on the three-dimensional assembly for each screw pair determined in step 103. The final screw position is based on an analysis of local and global stress maximums and minimums, to avoid placing excess stress on the system that could lead to screw pullout. Stress analysis may be performed through classical mathematical techniques, analytic mathematical modelling or computational simulation, experimental testing, or a combination of methods. Any needed correction is accomplished by returning to step 106 and repeating steps 106 to 110 a predetermined number of times. If, in step 113, it is determined that the predetermined number of iterations has been performed, the system may proceed to step 111 and carry out the operation. It is anticipated that the needed correction should be accomplished in the first repetition, and thus the number of predetermined iterations will be low.

Figures 2A, 2B, 2C, 2D, 2E, 2F, 2G, 2H:
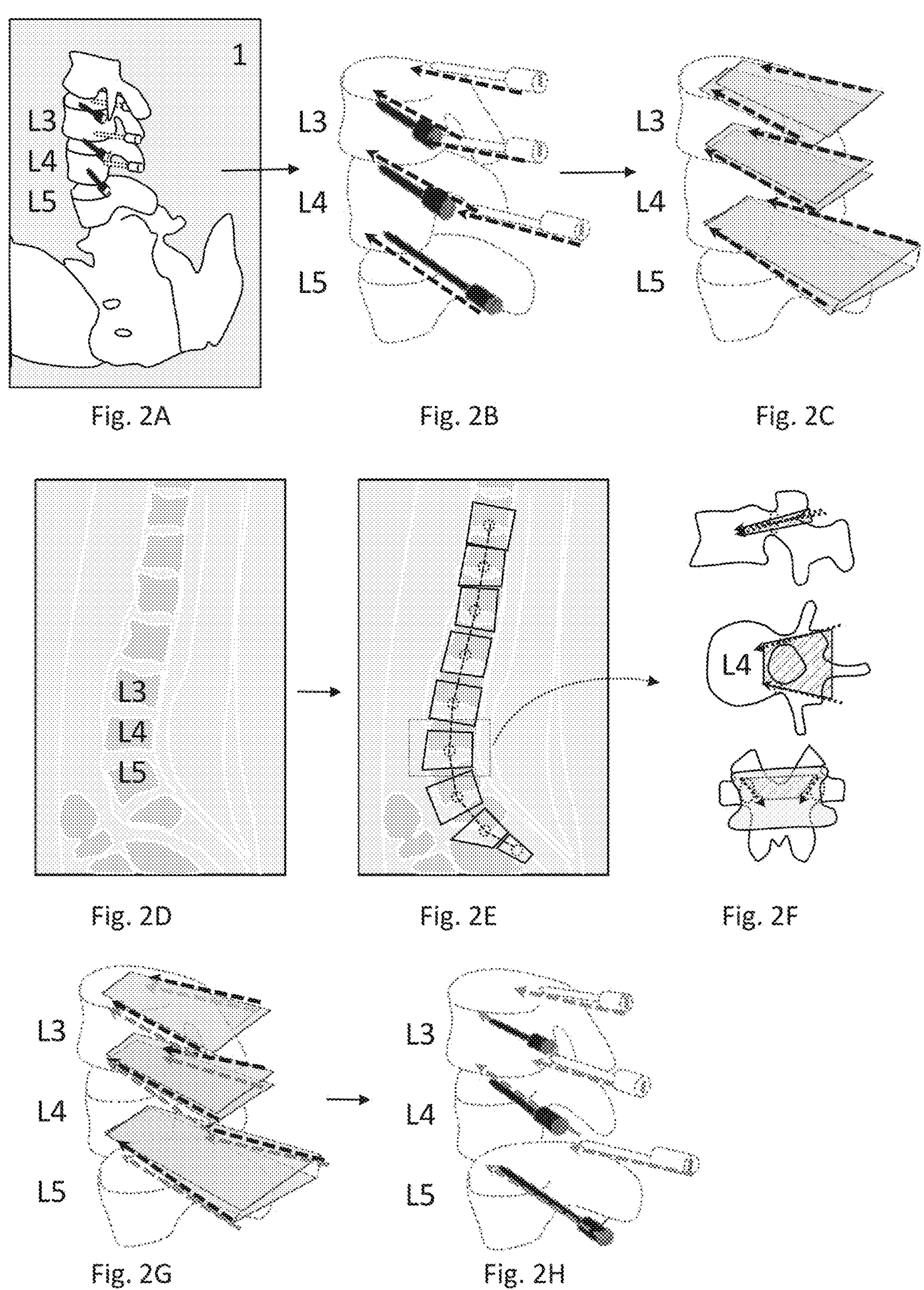
FIGS. 2A to 2H illustrate the manner in which the alignment is accomplished.

Reference is now made to FIGS. 2A-H, illustrating the steps of the method from FIG. 1 in an exemplary implementation of the present disclosure, in which the hardware elements are pedicle screws, and each vertebra to be instrumented has two pedicle screws. FIG. 2A illustrates steps 101 and 102, in which the preoperative images are obtained and analyzed in three dimensions to plan: a) at least some of the vertebral levels to be instrumented; b) the type, number and size of intervertebral rods and pedicle screws to be inserted; and c) the surgical approach.

In FIGS. 2B and 2C, corresponding to step 103, the planned position and orientation, i.e., the pose and length, of the screws (FIG. 2B) are determined, such that the path of each screw from entry point to its final position is identified. The spatial information for a pair of screws (black—left, white—right) is converted into a three-dimensional assembly (black arrows) providing both the position and angular direction as well as the length of both screws as a single entity relative to the vertebra into which they will be inserted (FIG. 2C). The three-dimensional assembly for a pair of screws (gray trapezoid) provides greater resolution, i.e., fewer degrees of freedom, than the essentially two-dimensional spatial information pertaining to a single screw. Each three-dimensional assembly may also be used in a full complement of assemblies, corresponding to the positions of the sum total of pedicle screws and other hardware in their final planned position as a bone-hardware construct.

In FIGS. 2D to 2F, at least one intraoperative three-dimensional image is acquired of the operative area (FIG. 2D), and subjected to an internal image segmentation process with feature identification using machine learning or other forms of artificial intelligence to identify the bony outlines and other anatomical features in the image (FIG. 2E), producing a three-dimensional outline of each vertebra to be instrumented (FIG. 2F), represented as a series of three two-dimensional outlines.

As shown in FIG. 2F, the three-dimensional representation of a vertebra is shown in three two-dimensional planes, lateral, superior-inferior, and frontal (anterior-posterior). On these processed images, the typical positions of pedicle screws are positioned, as in step 107. These outlines are matched to the preoperative images, and the three-dimensional assembly from the preoperative plan in step 106 superimposed on the outlines. In typical registration procedures, it may happen that anatomical elements of the patient may move relative to others, thereby introducing an element of uncertainty in the registration process. One of the advantages of this planning method relative to registration procedures is that the planned pose of the screws for each vertebra will not change relative to the individual vertebra into which it will be inserted, thereby eliminating the need for an external registration procedure and enabling a surgical plan with higher resolution.

In FIG. 2G, the three-dimensional assembly representing a screw pair (FIG. 2C) is superimposed as a single unit on the three-dimensional representations of each vertebra and matched to the planned screw poses from FIG. 2F (step 108) to illustrate the final, planned bone-hardware assembly from step 103. At this point, any mismatch between the intraoperative screw placements and the preoperative three-dimensional assemblies can be identified. Further, by superimposing the full complement of three-dimensional paired screw assemblies onto the intraoperative images on which the individual three-dimensional assemblies have been positioned for individual vertebrae, any mismatch due to movement of the patient's spine relative to the preoperative images, or relative to the planned surgical outcome, can be identified (step 109). Such mismatch of one vertebra relative to the adjacent vertebrae has the potential to cause either a) the path of the inserted screw to deviate from the planned path, or b) a misalignment of the corrected spinal alignment parameters. At this point of the method, the planned screw positions from FIG. 2F, which are input to the controller of the robotic surgical system for robotic screw insertion, can be adjusted as needed to correspond to the original plan shown in FIGS. 2A and 2B (steps 110 and 112). It may also be determined that the planned screw positions from FIG. 2F are different from the original plan but maintain the desired, corrected spinal alignment parameters, in which case the surgeon or the system may decide to implement the intraoperatively determined screw positions. With reference to FIG. 2H, once planned screw positions are have been determined, the plan may be updated to reflect the specific model of screw that will be inserted, and/or implemented using, for example, a system 300.

Figure 3:
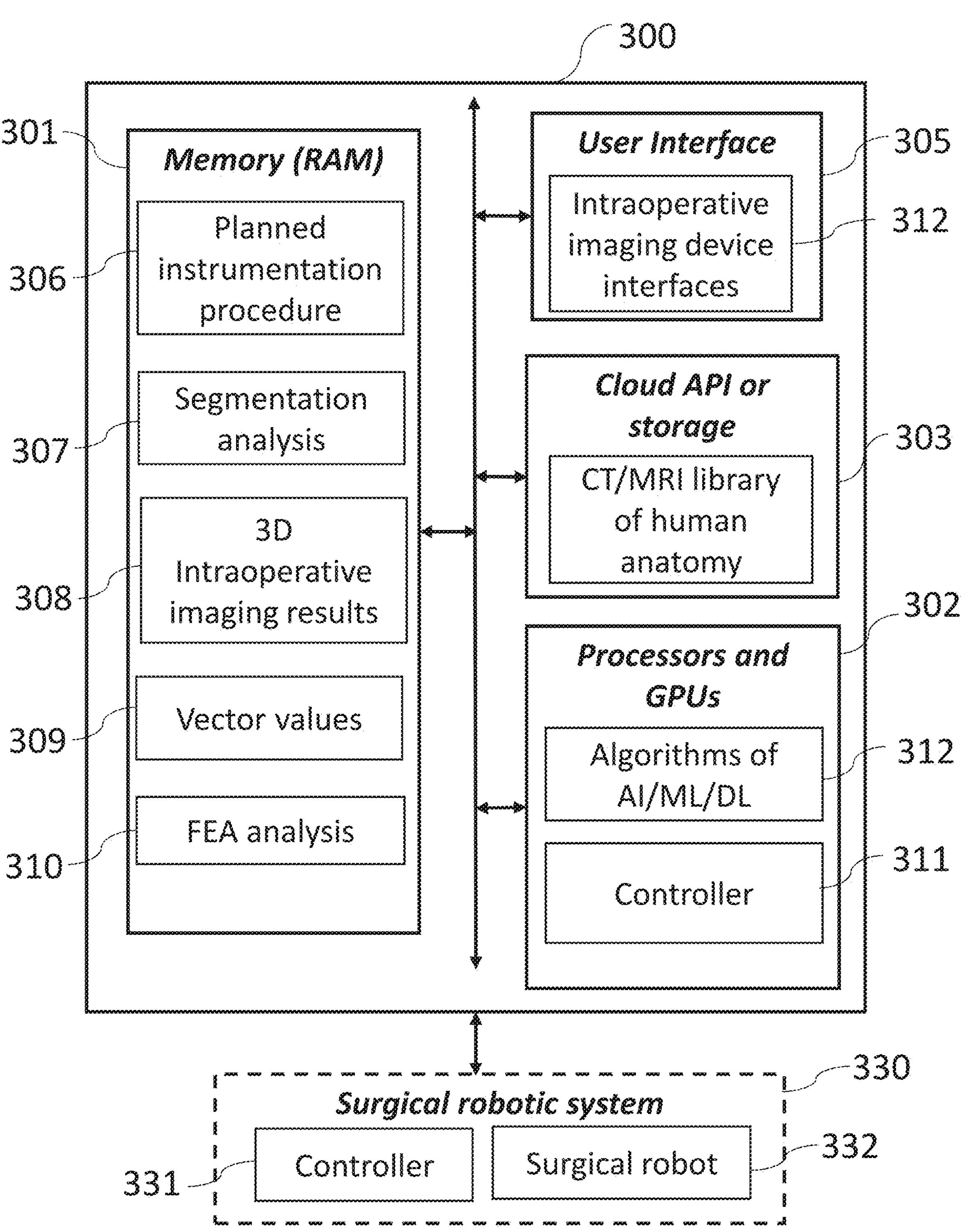
FIG. 3 schematizes the structural components of an exemplary block diagram of a system used to implement the disclosed methods.

Reference is now made to FIG. 3, illustrating an exemplary system 300 for implementing an embodiment of the disclosed methods, comprising a memory 301, at least one processor and graphics processing unit 302, a means of storage 303, and a user interface 305. The memory 301 further comprises the planned surgical procedure 306 from step 102, segmentation analysis 307 from FIG. 2D, the intraoperative imaging results 308 from FIG. 2C, stored paired segment values 309 from step 103, and in some implementations, finite element analysis results 310. The processor 302 comprises artificial intelligence algorithms 312 and a controller 311. The user interface 305 comprises interfaces for intraoperative imaging devices 312. The system 300 communicates with a surgical robotic system 330, comprising at least a controller 331 and a surgical robot 332.

In this disclosure, the term system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components, such as optical, magnetic, or solid state drives, that provide the described functionality; or a combination of some or all of the above, such as in a system-on-chip. The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this disclosure may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A system, comprising:

at least one processor executing instructions stored on at least one non-transitory storage medium, to cause the at least one processor to:

a) based on a surgical plan derived from preoperative images, define planned poses for implantable hardware elements comprising at least one three-dimensional implantable hardware element, or at least two two-dimensional implantable hardware elements, to be attached to or inserted into an anatomical part;

b) convert the planned poses into a three-dimensional geometric function for the anatomical part;

c) process at least one intraoperative three-dimensional image of the anatomical part to identify anatomical features to which the three-dimensional geometric function is to be aligned;

d) on the at least one processed intraoperative three-dimensional image, define a range of possible positions for the three-dimensional geometric function; and e) using the identified anatomical features, virtually align the three-dimensional geometric function in the at least one processed intraoperative three-dimensional image, the alignment achieving a position of the implantable hardware elements that is compatible with the surgical plan and has greater accuracy than aligning each implantable hardware element individually on the at least one processed intraoperative three-dimensional image, without the need to perform registration between the preoperative images and the at least one processed intraoperative three-dimensional image.

2. The system according to claim 1, wherein steps a) to e) are performed for a plurality of anatomical parts.

3. The system according to claim 2, further comprising steps:

f) repeat steps a) to e) on each anatomical part, such that a plurality of three-dimensional geometric functions is generated;

g) compare virtual alignments in the at least one processed intraoperative three-dimensional image of all three-dimensional geometric functions with the surgical plan; and h) if the virtual alignments in the at least one processed intraoperative three-dimensional image are inconsistent with the surgical plan, repeat step e), such that the positioning of the implantable hardware elements has greater accuracy than aligning each implantable hardware element individually on the at least one processed intraoperative three-dimensional image for a complete set of implantable hardware elements for the plurality of anatomical parts.

4. The system according to claim 1, wherein a robotic surgical system enabled to carry out the surgical plan uses at least one aligned three-dimensional geometric function in the at least one processed intraoperative three-dimensional image to update the surgical plan.

5. The system according to claim 1, wherein the preoperative images comprise at least one three-dimensional MRI or CT image.

6. The system according to claim 1, wherein virtually aligning the three-dimensional geometric function is based on one or more predetermined constraints corresponding to the anatomical features.

7. The system according to claim 1, wherein the surgical plan is for a spinal fusion, the implantable hardware elements are pedicle screws and intervertebral rods, and the anatomical part is a vertebra.

8. The system according to claim 1, wherein the three-dimensional geometric function defines a fixed angle between the at least two two-dimensional implantable hardware elements in reference to each other.

9. The system according to claim 1, wherein at least one form of artificial intelligence and anatomical images are used to identify a range of possible positions for implantable hardware elements within the at least one intraoperative three-dimensional image.

10. The system according to claim 1, further comprising the step of determining a mismatch in the planned poses of implantable hardware elements between the preoperative images and the at least one processed intraoperative three-dimensional image, wherein the determined mismatch is used to adjust the planned poses of the implantable hardware elements.

11. The system according to claim 1, wherein the virtual alignment reduces a stress cost function using an algorithm that identifies a stress minimum between one of the implantable hardware elements and the anatomical part.

12. The system according to claim 11, wherein the algorithm uses artificial intelligence applied to at least one of feature detection, intensity detection, finite element analysis with meshing, and image segmentation to reduce the stress cost function.

13. The system according to claim 12, wherein the three-dimensional geometric functions for all implantable hardware elements are positioned in combination with analysis of preoperative images showing motion analysis of the anatomical part.

14. The system according to claim 11, wherein the stress cost function further takes into account predicted stress of all implantable hardware elements on the anatomical part.

15. The system according to claim 1, wherein the surgical plan is for a spinal fusion, and the position of the implantable hardware elements is determined by analysis of measured spinal mobility limitations over substantial lengths of the patient's spine in order to plan a correction procedure with minimal surgical corrective steps.

16. The system according to claim 1, wherein the three-dimensional geometric function is defined as a mathematical quantity having four points, the four points representing the beginning and ending of each of a pair of pedicle screws for a given vertebra in three-dimensional space.

17. The system according to claim 16, wherein a first of the pair of pedicle screws is used after implantation in combination with the at least one processed intraoperative three-dimensional image to accomplish the virtual alignment with a second of the pair of pedicle screws.

18. The system according to claim 1, wherein the three-dimensional geometric function comprises the position, length, and angle of a right pedicle screw and a left pedicle screw having a fixed angle between them, for implantation into a single vertebra.

19. A system, comprising:

a memory for storing a surgical plan, which is based on preoperative images, for a region of interest, the surgical plan comprising planned poses of implantable hardware elements to be inserted into anatomical parts in the region of interest; and at least one processor having a controller to;

convert the planned poses into a three-dimensional geometric function for an anatomical part;

process at least one intraoperative three-dimensional image of the anatomical part to identify anatomical features to which the three-dimensional geometric function is to be aligned;

on the at least one processed intraoperative three-dimensional image, define a range of possible positions for the three-dimensional geometric function; and using the identified anatomical features, virtually align the three-dimensional geometric function in the at least one processed intraoperative three-dimensional image, the virtual alignment achieving a position of the implantable hardware elements that is compatible with the surgical plan and has greater accuracy than aligning each implantable hardware element individually on the at least one processed intraoperative three-dimensional image, without the need to perform registration between the preoperative images and the at least one processed intraoperative three-dimensional image.

20. A system, comprising:

at least one processor executing instructions stored on at least one non-transitory storage medium, to cause the at least one processor to:

a) based on a surgical plan derived from a preoperative images, define planned poses of a pair of pedicle screws for a vertebra;

b) convert the planned poses of the pair of screws into a three-dimensional geometric function for the pair of screws;

c) process at least one intraoperative three-dimensional image of the vertebra to identify surface features of the vertebra;

d) on the at least one processed intraoperative three-dimensional image, define a range of possible positions for each pedicle screw through vertebral pedicles; and e) using the identified surface features, virtually align the three-dimensional geometric function in the at least one processed intraoperative three-dimensional image, the virtual alignment achieving a position of the pedicle screws that is compatible with the surgical plan and reduces a cost function to a greater degree than aligning each pedicle screw individually on the at least one processed intraoperative three-dimensional image, without the need to perform registration between the preoperative images and the at least one processed intraoperative three-dimensional image.

* * * * *